United States Patent [19]

Noreen et al.

[11] Patent Number: 5,158,557
[45] Date of Patent: Oct. 27, 1992

[54] REFASTENABLE ADHESIVE TAPE CLOSURE

[75] Inventors: Allen L. Noreen, Lake Elmo; Dean R. Crissinger, Prescott; William L. Melbye; Eric G. Rodgers, both of St. Paul; Alan J. Sipinen, Maplewood; Leigh E. Wood, Woodbury, all of Minn.

[73] Assignee: Minnesota Mining and Manufacturing Company, St. Paul, Minn.

[21] Appl. No.: 622,180

[22] Filed: Dec. 3, 1990

Related U.S. Application Data

[63] Continuation of Ser. No. 177,494, Apr. 4, 1988, abandoned.

[51] Int. Cl.⁵ .......................... A61F 13/05; B32B 3/00
[52] U.S. Cl. ..................................... 604/389; 428/156
[58] Field of Search ............... 604/372, 389, 390; 428/40, 147, 156, 162, 172, 351, 352, 338

[56] References Cited

U.S. PATENT DOCUMENTS

| Re. 24,906 | 12/1960 | Ulrich | 526/328 |
|---|---|---|---|
| 3,484,835 | 12/1969 | Trounstine et al. | 161/130 |
| 3,630,201 | 12/1971 | Endres . | |
| 3,853,129 | 12/1974 | Kozak . | |
| 3,867,940 | 2/1975 | Mesek et al. | 128/287 |
| 4,023,570 | 5/1971 | Chinai et al. . | |
| 4,074,004 | 2/1978 | Bateson et al. | 428/504 |
| 4,127,693 | 11/1978 | Lemelson | 428/167 |
| 4,163,077 | 7/1979 | Antonsen | 428/355 |
| 4,237,889 | 12/1980 | Gobran | 128/287 |
| 4,343,848 | 8/1982 | Leonard, Jr. | 428/156 |
| 4,349,598 | 9/1982 | White | 428/161 |
| 4,397,905 | 8/1983 | Dettmer et al. | 428/180 |
| 4,413,109 | 11/1983 | Haas | 428/156 |
| 4,436,520 | 3/1984 | Lipko et al. | 604/385 |
| 4,476,593 | 10/1984 | Fanselow et al. | 5/417 |
| 4,518,643 | 5/1985 | Francis | 428/156 |
| 4,536,362 | 8/1985 | Donaldson | 264/171 |
| 4,543,139 | 9/1985 | Freedman et al. | 156/152 |
| 4,546,029 | 10/1985 | Cancio et al. . | |
| 4,576,850 | 3/1986 | Martens | 428/156 |
| 4,588,258 | 5/1986 | Hoopman | 350/103 |
| 4,609,584 | 9/1986 | Cutler et al. | 428/156 |
| 4,643,730 | 2/1987 | Chen et al. | 604/390 |
| 4,645,501 | 2/1987 | Teed | 604/390 |
| 4,655,761 | 4/1987 | Grube et al. | 604/389 |
| 4,710,190 | 12/1987 | Wood et al. | 604/389 |
| 4,728,325 | 3/1988 | Spiller | 604/389 |
| 4,769,283 | 9/1988 | Sipinen et al. | 428/40 |
| 4,861,635 | 8/1989 | Carpenter et al. | 428/517 |

FOREIGN PATENT DOCUMENTS

| 0205289 | 12/1986 | European Pat. Off. . |
| 0316601 | 5/1989 | European Pat. Off. . |
| 3338201 | 10/1983 | Fed. Rep. of Germany . |
| 2104847 | 3/1983 | United Kingdom . |

*Primary Examiner*—Randall L. Green
*Assistant Examiner*—K. Reichle
*Attorney, Agent, or Firm*—Gary L. Griswold; Walter N. Kirn; Carole Truesdale

[57] ABSTRACT

A refastenable adhesive closure is provided. The closure has a pressure-sensitive adhesive-bearing fastening tab and a target portion, or target strip, having a working face for contact with the adhesive-bearing fastening tab. The working face of the target strip is formed with peaks and valleys, the height of the peaks above the valleys being substantially uniform and from about 40 to 300 μm, the spacing between adjacent peaks being from about 50 to 500 μm, the back face of the target portion being substantially flat, and the thickness of the adhesive layer of the tab being no more than about 90% of the height of the peaks above the valleys. The closure is resistant to contamination by dust and other fine particulate matter and is especially useful for refastenable disposable diaper closures and refastenable envelope closures.

28 Claims, 4 Drawing Sheets

REFASTENABLE ADHESIVE TAPE CLOSURE

BACKGROUND OF THE INVENTION

1. Field of the Invention

The invention relates to refastenable pressure-sensitive adhesive closures of diapers and other articles such as envelopes, especially the target strips of the adhesive closures The invention is particularly concerned with the problem that such closures tend to lose their adhesiveness prematurely because of contamination.

2. Description of the Related Art

U.S. Pat. No. 4,163,077 (Antonsen et al.) attributes much of the present commercial success of disposable diapers to pressure-sensitive adhesive tape closure systems which replace safety pins, but says that contamination by talcum powder can greatly reduce the ability of the adhesive to adhere. The Antonsen patent answers this problem by using as the pressure-sensitive adhesive a rubbery block copolymer which is said to display good adhesion and shear properties even when contaminated with fine particulate material, e.g., talcum powder. In spite of the availability of such a pressure-sensitive adhesive, one of the most common complaints about disposable diapers is the failure of the adhesive tape closure, and it is believed that such failures primarily occur because of talcum powder contamination.

A refastenable diaper closure can be more resistant to contamination when it employs a more aggressive pressure-sensitive adhesive which when contaminated would lose some tackiness but still be sufficiently tacky to hold the diaper in place. If made too aggressive, a closure would be difficult to open when not contaminated, especially by persons who do not have strong fingers. There also is a hazard that the diaper might be torn upon opening an adhesive tape closure if adhesive is overly aggressive.

Other than the Antonsen patent, we are not aware of any prior teaching about how to minimize failures of refastenable adhesive diaper closures However, there are a number of publications about improving those closures in other respects. U.S. Pat. No. 4,237,889 (Gobran) concerns the problem that prior tape tabs would often tear, or if made not to tear, would either be too expensive or so stiff that a baby's tender skin might be injured. The Gobran patent answers this problem by using as the backing of the tab a crystalline polypropylene film having one smooth face and one specially textured face.

U.S. Pat. No. 4,436,520 (Lipko et al.) discloses that the outer or back sheet of a disposable diaper typically is embossed to reduce gloss, but that "the embossing materially reduces the adhesion of the embossed surface for the closure tabs so that the diaper is no longer secure in its use on the infant" (col. 1, lines 19-22). The Lipko patent further discloses that in embossed films of polyethylene having a (45°) gloss of no greater than 8, the adhesion of the embossed surface is markedly enhanced when the surface has a mean value of maximum profile height of less than 150 and maximum peak to valley height of less than 230 as measured using a Surtronic 3 apparatus.

While the embossing height of the outer sheet of a disposable diaper typically is from 20 to 30 $\mu$m, U.S. Pat. No 3,484,835 (Trounstine et al.) discloses a plastic film having a permanently embossed design which simulates a plain woven fabric for uses including the outer sheet of a disposable diaper where the embossing height is about 3 to 4 times the thickness of the film e.g., 75 to 100 $\mu$m for a 25 $\mu$m film.

U.S. Pat. No. 4,645,501 (Teed) points out that it is desirable to be able to unfasten and reposition the adhesive fastener tabs of disposable diapers but that because of the need for a strong bond between the fastener tab and the outer plastic sheet of the diaper, the fastener tab cannot generally be removed from the surface of the plastic sheet without tearing and pulling away the thin water-impervious plastic outer cover of the garment. To prevent the tearing of the outer cover, diapers often are made with a plastic reinforcing strip (sometimes called a "target strip") covering areas that can be contacted by the fastener tabs. The Teed patent avoids the need for a reinforcing strip while attaining repositionability by employing as the water-impervious plastic cover or outer sheet one that is embossed to have ridges or ribs that are separated by square recessed surface portions having downwardly tapering sides. In Example I, the plastic outer sheet is one mil (25 $\mu$m) in thickness and has a recessed depth of 0.0023 inch (58 $\mu$m).

Among publications concerning reinforcing or target strips for disposable diapers are U.S. Pat. No. 3,867,940 (Mesek et al.) which discloses a scrim reinforced backing sheet for disposable diapers; West German Offenlegungsschrift No. DE 3338201 A1 (Molnlycke AB) discloses a nonelastic target strip of polyester; and European Patent Publication No. 0 080 647 A1 (Boussac Saint Freres) which discloses reinforced areas on the front of a disposable diaper, the reinforced areas being, for example, a smooth-surfaced film of polypropylene adhered to the outer sheet by a layer of adhesive.

In U.S. Pat. No. 4,643,730 (Chen et al.), a reinforcing strip is provided on the inner face of the outer or backing sheet of a disposable diaper by coating the sheet with a high-energy-radiation curable coating and curing the coating.

U.S. Pat. No. 4,543,139 (Freedman et al.) discloses refastenable adhesive closures for packages and particularly concerns the problem of such closures becoming ineffective due to contamination, mentioning oils and small food particles. The Freedman closure has two pressure-sensitive adhesive strata, one forming a strong bond to the body of a package and a second forming a relatively weak bond permitting it to be separated from the cover of the package. In the course of reclosing and reopening the package, the strong adhesive becomes mixed with the weak adhesive, thereby offsetting contamination encountered while the closure is open.

U.S. Pat. No. 4,655,761 (Grube et al.) discloses a disposable diaper with a refastenable tape system which utilizes a polypropylene tape material that is embossed on the outer surface and smooth on the adhesive-carrying surface. The adhesive on the tape is a semihard adhesive that provides high adhesion values to the polymer that nevertheless may be peeled away and refastened. The polymer forming the outer backing of the diaper is a relatively thick, embossed polymeric sheet.

U.S. Pat. No. 4,710,190 (Wood et al.) discloses a diaper having an improved reinforced area for receiving adhesive fastening tape. The diaper includes an outer liquid-impermeable film and a bilayer film bonded to the liquid-impermeable film as a peel-resistant reinforced fastening area. The bilayer film comprises a reinforcing layer and a room-temperature-nontacky bonding layer, the bonding layer holding the reinforcing layer to the liquid-impermeable film with greater force than that which the fastening tape applies when adhered to the top of bilayer film.

U.S. Pat. No. 4,397,905 (Dettmer et al.) discloses an adhesive tape which has a support film of a synthetic thermoplastic polymer and an adhesive layer on one side, the support film having a thickness of less than about 35 μm and having provided on the nonadhesive surface elevations having a depth within a range of from about 5 to 20 μm.

U.S. Pat. No. 4,536,362 (Donaldson) discloses a method for producing longitudinally ribbed plastic film which includes extruding through a pair of die lips, at least one of which is provided with slots which run at an angle to the direction of resin flow across the die lips. Impurities in the resin, such as gel particles, collect in the slots of the die lip and are extruded in the thickened, rib portion of the film. The ribs form strengthened areas which hinder the propagation of tears and punctures.

U.S. Pat. No. 4,349,598 (White) discloses a retroreflective film having an array of light-reflecting right triangle prisms between a transparent surface layer and a backing layer. U.S. Pat. No. 4 588 258 (Hoopman) discloses cube-corner retroreflective articles having improved angularity along multiple viewing planes, the articles comprising at least one matched pair of cube-corner retroreflective elements which are rotated 180° with respect to one another, the three lateral mutually perpendicular faces of the elements being defined at their bases by linear edges that lie in a common plane, and the optical axes of the elements being tilted toward one another.

U.S. Pat. No. 4,576,850 (Martens) discloses an article comprising a shaped, plastic, monolithic layer, or body, comprising crosslinked polymer with hard and soft segments of moieties and having a microstructure-bearing surface which is prepared by a process comprising filling a mold master, bearing or encoded with the microstructure to be replicated, with a fluid, castable, one-part, radiation addition-polymerizable crosslinkable, synthetic, organic oligomeric composition having hard segments and soft segments, exposing the resulting cast composition to radiation, and thereby forming the article. The article may be, for example, a retroreflective cube-corner sheeting, Fresnel lens or video disc.

U.S. Pat. No. 4,476,593 (Fanselow et al.) discloses a tanning blanket having a plurality of incremental reflectors in a Fresnel pattern on a flexible substrate, which reflectors reflect incident solar radiation toward the person and distribute the reflected radiation across the flanks of the person.

European Patent Publication No. 0 205 289 Minnesota Mining and Manufacturing Company) discloses a conformable drag reduction article, typically a film, having a patterned surface capable of reducing drag resistance by fluid flowing thereover on a first side and an adhesive on a second side, the second side being parallel to the first side.

Refastenable pressure-sensitive adhesive closures are also widely used on envelopes such as are commonly used for interoffice mail. Although such envelopes may be designed to be used up to about 30 times before being discarded, their closures tend to become contaminated and to lose their adhesiveness in less than ten mailings

SUMMARY OF THE INVENTION

The present invention relates to refastenable adhesive closures resistant to contamination by fine particulate matter comprising a pressure-sensitive adhesive-bearing fastening tab and a target portion, or target strip, having a working face for contact with the adhesive-bearing fastening tab wherein the working face of the target portion is formed with peaks and valleys, the height of the peaks above the valleys is substantially uniform and from about 40 to 300 μm, the spacing between adjacent peaks is from about 50 to 500 μm, the back face of the target strip is substantially flat, and the thickness of the adhesive layer of the tab is no more than about 90% of the height of the peaks above the valleys.

The target portion of the refastenable pressure-sensitive adhesive closure of the invention may optionally be provided with intermittent small protrusions in the valleys to reduce tear propagation.

The invention also relates to a roll of tape useful for preparing the target portion of the closure of claim 1, the tape comprising a flexible polymeric substrate having a working face and an adhesive-bearing face, the working face having saw-toothed ridges, the height of said ridges above the substrate being substantially uniform and from about 40 to 300 μm, the spacing between adjacent ridges being from about 50 to 500 μm, the ridges having first and second faces parallel to or transverse to, preferably parallel to, the direction in which the tape is rolled, the first transverse face being substantially orthogonal to the substrate, and the face bearing the adhesive being substantially flat.

The invention further relates to a disposable diaper comprising a water-impermeable cover sheet and a water-permeable inner sheet and absorbent layer between the cover sheet and the inner sheet, the diaper having front and back end portions with the back portion having ears protruding therefrom, target portions on the front portion of the cover sheet, and attached to each ear, a pressure-sensitive adhesive-bearing fastening tab, the target portions having a working face for contact with the adhesive-bearing fastening tab, wherein the working face of the target strip is formed with peaks and valleys, the heights of the peaks above the valleys being substantially uniform and from about 40 to 300 μm, the spacing between adjacent peaks being from about 50 to 500 μm, the back face of the target portion is substantially flat, and the thickness of the adhesive layer of the tab is no more than about 90% of the height of the peaks above the valleys. The entire outer cover of the diaper, as well as the working face of the target portion may comprise peaks and valleys.

The invention still further relates to an envelope or package comprising a body and a flap, the flap bearing a pressure-sensitive adhesive-bearing fastening tab and the body bearing a target portion having a working face for contact with the adhesive-bearing fastening tab, wherein the working face of the target strip is formed with peaks and valleys, the height of the peaks above the valleys being substantially uniform and from about 40 to 300 μm, the spacing between adjacent peaks being from about 50 to 500 μm, the back face of the target portion is substantially flat, and the thickness of the adhesive layer of the tab is no more than about 90% of the height of the peaks above the valleys.

The pressure-sensitive adhesive closure of the invention, when used to provide refastenable diapers, is believed to be substantially more resistant to contamination by talcum powder than the adhesive closures presently available. The novel pressure-sensitive adhesive closure also provides refastenable envelopes and other packages and is believed to be more resistant to contamination by dust, dirt, and other fine particulate matter than is any refastenable adhesive closure presently available for envelopes and packages In any of these uses, the refastenable adhesive closure of the invention experiences surprisingly little loss in adhesion when contaminated by fine particulate material.

DETAILED DESCRIPTION OF THE INVENTION

Figure 2:
FIGS. 1-7 are photomicrographs at 250 X of the working face of target strips that can be used in refastenable pressure-sensitive adhesive closures of the invention.
Figure 4:
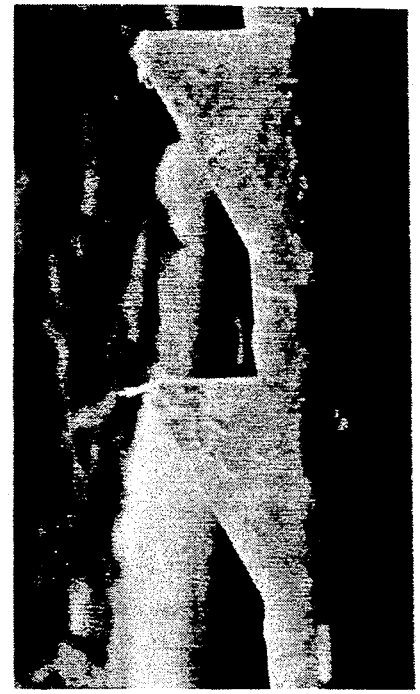

The surface area of the peaks and valleys of the working face of the target strips is preferably at least 35% more than that of a flat surface, disregarding asperities less than about 10 μm in height. Preferably, the thickness of the adhesive layer of the fastening tab is at least about 25% of the height of the peaks, and no more than 90% of the height of said peaks above said valleys, more preferably from about 50 to 80%. When the thickness of the adhesive layer is below about 50%, the novel adhesive closure might fail in some uses, especially in shear. When the thickness of the adhesive layer is above about 80%, the novel adhesive closure would be less resistant to contamination by talcum powder and other particulate contaminants.

The novel target strip is preferably formed from a thermoplastic material and is preferably cast or profile extruded rather than embossed If embossed, the contours in the back face must be filled or the back face must be laminated to some sort of web to make the back face substantially flat, i.e., sufficiently flat to obfuscate the peaks When the back face is made flat or originally is flat, the lateral support thus provided at the bases of the peaks should prevent the peaks from collapsing when the closure is refastened. Because casting or profile extrusion ensures that the target strip is solid beneath its peaks, the peaks at the face of a cast target strip may better maintain their shape as compared to an embossed target strip that has been made smooth at its back face. Furthermore, it is easier to attain a desired contour at the face of a target strip by casting or profile extrusion than by embossing.

Both the surface configuration of peaks and valleys on the target portion of the closure and the thickness of the adhesive layer on the fastening tab being no more than 90% of the height of the peaks above the valleys contribute to the contamination resistance of the closure. It is believed that the adhesive layer contacts only a portion of the peaks of the contaminated target portion of the closure on fastening leaving sufficient uncontaminated adhesive for good adhesion on subsequent refastening.

The crown of each peak preferably forms an angle of less than about 90°, more preferably from about 30° to 80° in order to facilitate penetration of the adhesive layer into the fastening tab. Good penetration enhances the adhesion values of the novel closure. The peaks of an especially useful target strip of the invention form saw-toothed ridges, each extending across the full width of the target strip transversely to the direction of removal of the fastener tab, with one face of each ridge extending substantially orthogonally to said direction and the other face being sloped from the peak generally in said direction. By "substantially orthogonal" is meant an angle of from 70° to 110°.

When the open angle between each steep face of the ridge and the direction of removal of the refastenable adhesive closure is less than 70°, the closure may have low shear strength When the open angle is greater than 110°, the peaks may tend to collapse when the fastening tab is pressed into the target portion.

When the crowns of the peaks are sharp, the closure exhibits significantly better resistance to failure in shear than does a closure which is substantially identical except for having rounded peaks. For diaper closures, sawtooth ridges should be oriented oppositely at the two ends of the target strip.

In a preferred embodiment of the invention, the surfaces of the peaks and valleys, the macrosurface of the working surface of the target strip, has superimposed thereon a microtopography comprising a large number of closely spaced asperities that have a jagged appearance when viewed at a magnification of about 500 X and are 2 to 30 μm in height and no more than 20% of the height of the peaks. Microtopographical measurements of such a surface, when present on a flat, i.e., having no peaks and valleys, can be made using a Perthometer TM profilometer. Generally, measurements made on a flat film using this profilometer, equipped with a stylus 5 μm in radius, are preferably in the ranges of $R_a$ of from 0.5 to 6 μm,
$S_m$ of from 50 to 200 μm,
$L_o$ of from 1.01 to 1.15, and
$S$ of from 60 to 400/cm, wherein $R_a$ = arithmetical mean deviation of the profile,
$S_m$ = mean spacing of the profile irregularities,
$L_o$ = relative length of the profile, and
$S$ = number of peaks per cm that exceed 0.1 μm in height.

Figure 8:
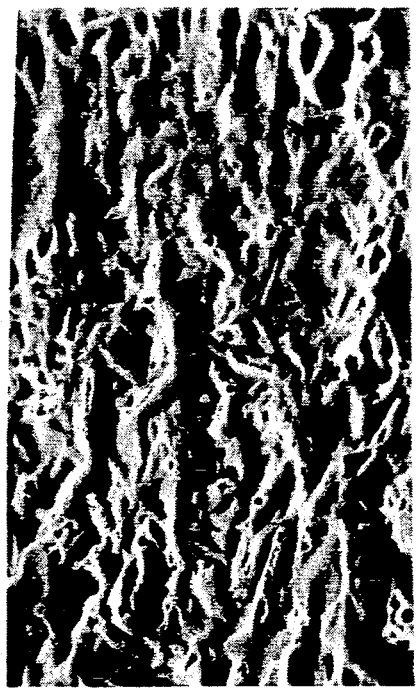
FIG. 8 is a photomicrograph at 500 X of a preferred microtopography useful in the refastenable pressure-sensitive adhesive closures of the invention.

Such microtopography is shown in FIG. 8.

Because a tear might propagate along sharp corners at the bases of the peaks of a sawtooth pattern, small protrusions, or rip-stops can be formed in the valleys that may extend from about 30 to 100% of the height of the peaks and preferably are spaced from adjacent rip-stops by from about 0.2 to 6 mm. In producing and handling long lengths of sheet material from which individual target strips are cut, such rip-stops make the sheet material more resistant to forces that might cause a tear to propagate such as the force required to unwind a roll of sheet material bearing a pressure-sensitive adhesive layer When the target sheet material bears a heat-activatable adhesive or an adhesive is not applied until a diaper is being formed, there should be less need for rip-stops. On the other hand, rip-stops may be useful in preventing tear propagation that could possibly arise from shear forces encountered while a diaper is being worn or a package is being handled The peaks and valleys may form a variety of contours. The contour illustrated in the above-cited Teed patent can be used but is not preferred because its peaks are symmetrical. To convert the Teed contour to a preferred contour, the faces of the peaks that are away from the direction of removal preferably are substantially orthogonal to said direction. More preferably, the open angle between those faces and the direction of removal is from about 70° to 90°. In another useful contour, the peaks are formed by a number of cylindrical or rectangular columns, each preferably larger at the base than at the crown. Useful columns include pyramids and cones.

In each of FIGS. 1-4, the peaks of the target strip form sawtooth ridges, each extending across the full width of the target strip transversely to the direction of removal of the fastener tab. One face of each peak extends substantially orthogonally to a plane defined by the crowns of the peaks, and the other face is sloped The target strips of FIGS. 1 and 3 were cast onto a steel cylinder and the target strips of FIGS. 2 and 4 were cast onto an aluminum cylinder The roughness at the crowns of the peaks of FIG. 2 indicates that the surface of the casting cylinder was not as well replicated as in FIG. 1, apparently because the polypropylene cooled before completely filling the casting cylinder.

Figure 1:
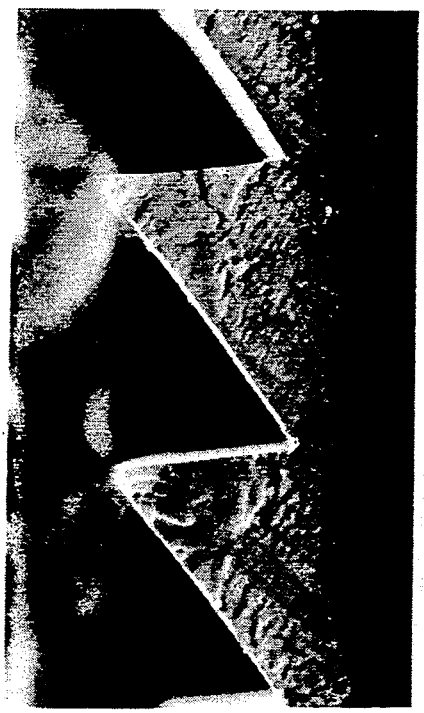
Figure 3:
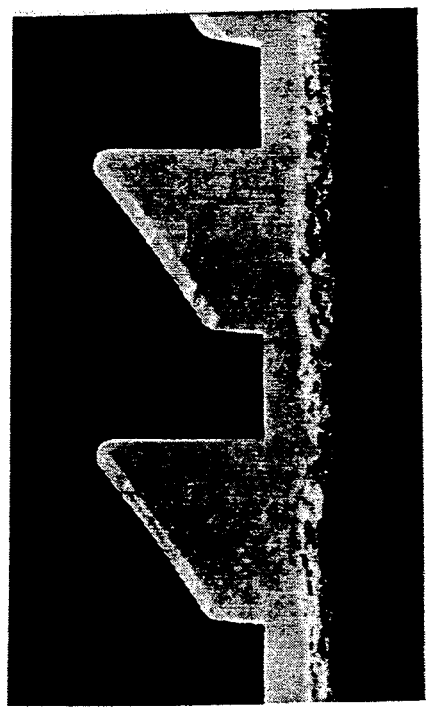
Figure 5:
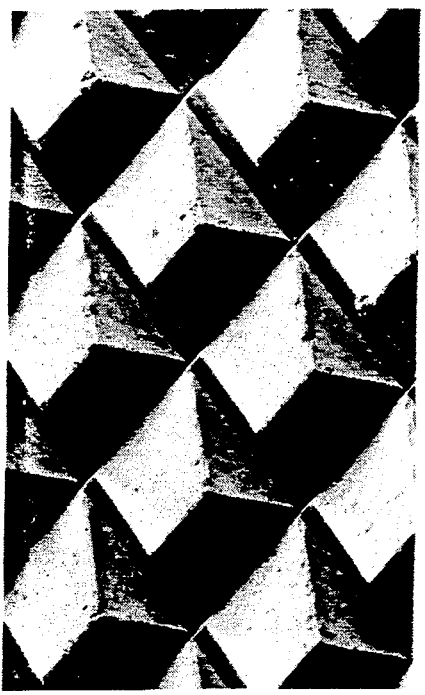

The target strip of FIG. 5 has a pattern of peaks and valleys similar to that of FIG. 1 except for grooves extending orthogonally to the sawtooth ridges.

Figure 6:
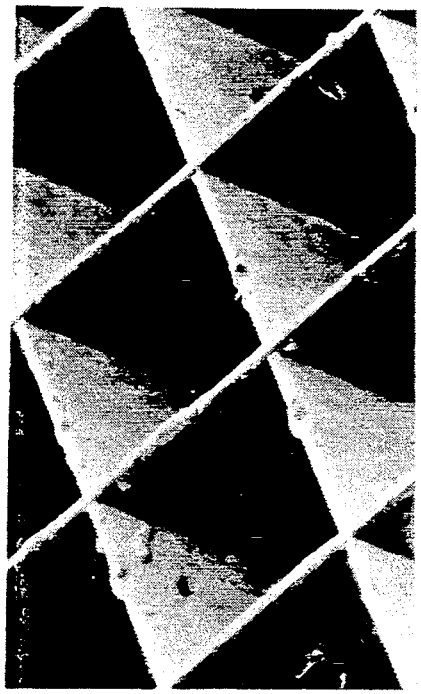

The target strip of FIG. 6 has a pattern of peaks and valleys generally similar to that of the above-discussed Teed U.S. Pat. No. 4,645,501.

Figure 7:
Figure 9:
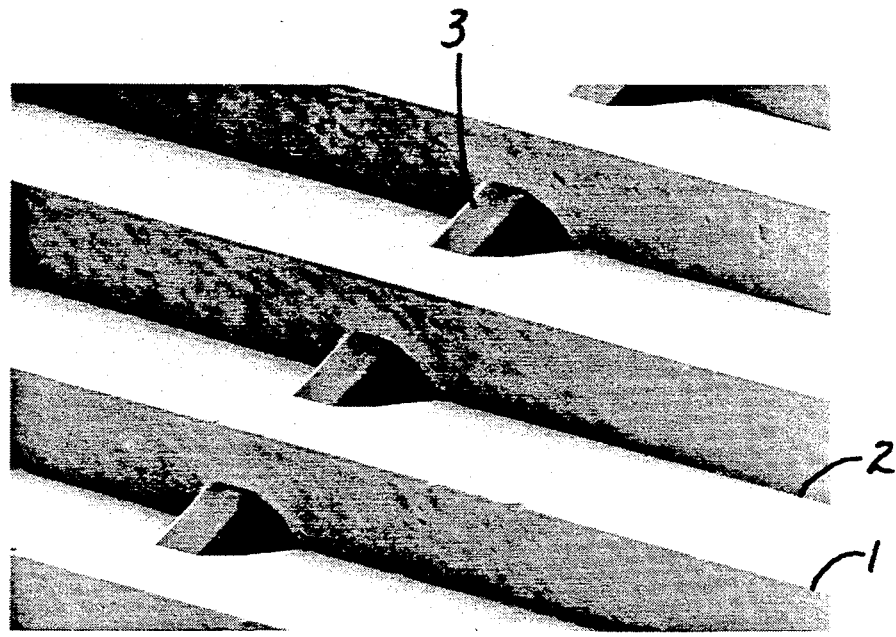
FIGS. 9 and 10 are photomicrographs at 280 X of the working face of target strips that can be used in the refastenable pressure-sensitive adhesive closures of the invention.
Figure 10:
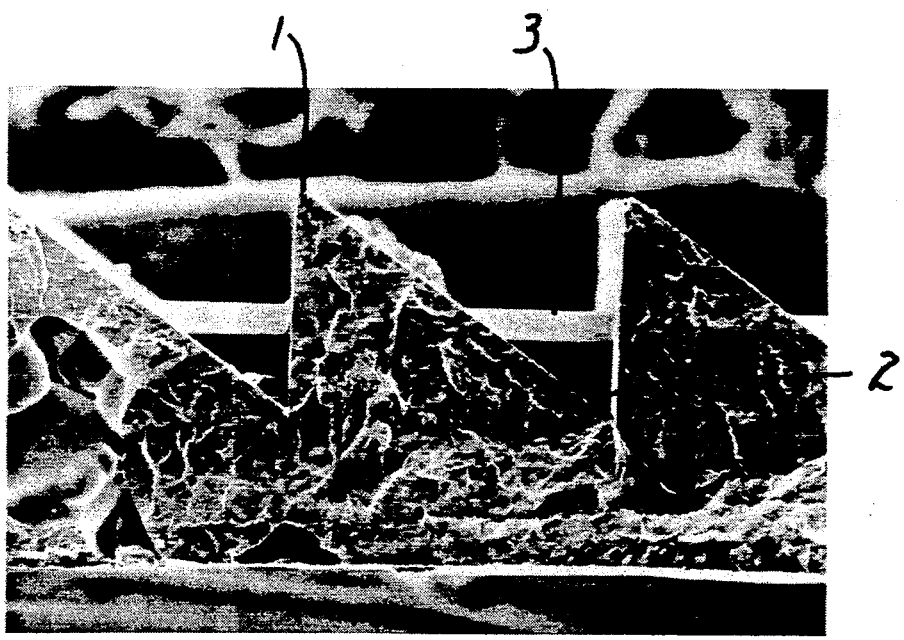

The target strip of FIG. 7 has a pattern of peaks in the form of columns that are larger at the bases than at the peaks and have rounded peaks The target strips of FIGS. 9 and 10 have a pattern of peaks 1 and valleys 2 with protrusions, or rip-stops, 3 provided to reduce tearing.

Because the back face of the target strip is substantially flat, an adhesive coated onto the back face can be sufficiently smooth to permit the novel target strip to be bonded permanently to a substrate such as an envelope or the outer sheet of a diaper. Pressure-sensitive adhesives and hot melt adhesives which are well-known in the art can be used.

Individual target strips of the invention preferably are cut from a long roll of material which is wound upon itself in roll form for convenient storage and shipment. When that material has been precoated with a layer of pressure-sensitive adhesive, there should be no need to employ a low-adhesion backsize when the adhesive layer is sufficiently thin (e.g., from about 12 to 25 $\mu$m) to contact only the crowns of the peaks. It is desirable to avoid a low-adhesion backsize, because that could interfere with forming a sufficient bond between the target strip and the adhesive fastening tab of the novel reclosable adhesive closure.

In diaper use, the novel target strip should be thin to avoid undesirable stiffness. The thickness of the target strip at the bases of the valleys preferably is within the range from about 15 to 50 $\mu$m, more preferably from about 20 to 35 $\mu$m. When used as a closure for an envelope or package, the same thicknesses are preferred for reasons of economy of raw material Also, sheet material for target strips up to about 50 $\mu$m thick at the bases of the valleys can be cast at line speeds faster than can thicker strips On the other hand, sheet material that is thinner than about 15 $\mu$m at the bases of the valleys might be too weak to be handled at high speeds The adhesive layer may be provided as a single adhesive strata or as a plurality of superposed and firmly united adhesive strata as disclosed in U.S. Pat. No. 4,260,659 (Gobran) which is incorporated herein for that purpose.

The target strip of the refastenable adhesive closure can be formed from any of the thermoplastic materials well known to be suitable for extrusion or embossing such as, for example, polyolefins, polyesters, polyamides, polyvinyl chloride, polycarbonate, polystyrene, and cellulose acetate butyrate The target strip of the refastenable adhesive closure preferably is formed from a polyolefin, especially polypropylene, polyethylene, blends and/or copolymers thereof, and copolymers of propylene and/or ethylene with minor proportions of other monomers such as ethylene/vinyl acetate, ethylene/acrylic acid, ethylene, and methacrylic acid. Polypropylene and propylene/ethylene copolymers are preferred for their combination of processability and physical properties. The melt flow index of these polypropylene or the propylene/ethylene copolymer is generally from about 10 to 100 grams/10 min., more preferably about 20 to 50 grams/10 min. The propylene/ethylene copolymers are preferred when toughness and ductility are especially important. Toughness, and ductility can be further increased by blending with polypropylene or propylene/ethylene copolymer minor proportions of low-density polyethylene or a copolymer of ethylene and a minor proportion of, for example, vinyl acetate, acrylic acid, or methacrylic acid providing that its molecular weight is chosen to be compatible with the base polyolefin.

A particularly preferred polyolefin for forming a target strip for use on disposable diapers is a blend of about 50 to 80 weight percent ethylene/propylene copolymer having a melt flow index of about 10 to 100 g/10 min, preferably about 20 to 50 g/10 min, and 20 to 50 weight percent low density polyethylene having a melt index of about 1 to 50 g/10 min preferably about 1 to 20 g/10 min. When the amount of low density polyethylene is below about 20 weight percent, the target strip may lack sufficient impact strength When the amount of low density polyethylene is greater than about 50 weight percent, the target strip may lack sufficient tensile strength A preferred polypropylene homopolymer for the target strip is Escorene TM PP-3085 from Exxon Chemical Co. It has a melt flow index of 35 g/10 min. A preferred propylene/ethylene random copolymer is Dypro TM 283-9-1 from Fina Oil and Chemical Co. with a melt flow index of 20 g/10 min. A preferred propylene/ethylene impact copolymer is WRS-7-319 available from Shell Chemical Co. with a melt flow index of 35 g/10 min. A preferred polyethylene is Tenite TM 1550 P LDPE available from Eastman Chemical Company with a melt flow index of 3.5 g/10 min. and density of 0.918.

The above-described polyolefins readily replicate a casting surface and also are readily profile extruded. They are tough, durable, and hold their shape well, thus making them easy to handle after being cast. Other thermoplastic resins which are equal in these respects are currently much higher in cost. Alternatively, the resin of the target strip can be cast from curable material, such as acrylates, polyester/acrylates, and polyurethane/acrylates, styrenes, and epoxies, and cured by exposure to heat, actinic radiation, such as ultraviolet radiation, or ionizing radiation such as electron beam radiation.

Polyolefin polymers can be extruded at a melt temperature of about 245° C. to 305° C., more preferably about 260° C. to 290° C., through a slot extrusion die and then into a nip between a rubber covered roll and a water cooled engraved metal casting roll. The casting roll temperature may be from about 40° C. to 95° C., more preferably about 50° C. to 80° C., depending upon resin composition, roll contact time, and desired tensile/tear properties. The roll contact time can be from about 0.1 to 1.0 second depending upon roll size, line speed, composition, and desired tensile/tear properties. In general, a short roll contact time requires lower casting roll temperatures and a long contact time requires higher roll temperatures to achieve the same degree of replication and physical properties.

The thickness of the layer of pressure-sensitive adhesive on the fastening tab of the novel adhesive closure preferably is from 15 to 70 μm. Greater thickness would be wasteful of raw material, both as to the amount of adhesive and as to the amount of material used in making the target strip. At adhesive thicknesses less than 15 μm, the tabs might not become sufficiently strongly adhered to the target strip.

The pressure-sensitive adhesive of the fastening tab preferably is sufficiently soft that under fingertip pressure, it is penetrated by the peaks so that from about 20 to 70% of the surface area of the peaks and valleys contacts the adhesive. At the same time, the adhesive should be sufficiently firm to provide good 135° peel value and shear value in the tests outlined below. A class of pressure-sensitive adhesives which provides these values is blends of 1) an AB block copolymer wherein A comprises vinylarene, B comprises a polymer of at least one monomer selected from conjugated dienes and alkenes, and A comprises from about 8 to 50 weight percent of the block copolymer, and 2) tackifying resin, the AB copolymer comprising from about 20 to 60 weight percent of total AB copolymer plus tackifier. Preferably the composite Tg of the B phase of the blend and the tackifying resin is from about 250° to 275° K., more preferably about 257° K. to 267° K.

The Tg of the B phase of the blend of AB block copolymer and tackifying resin can be calculated using the Fox equation and the Tg of each component, i.e., the Tg of the B block of the block copolymer and the Tg of each tackifying resin in the blend. The Fox equation is $$1/\text{composite Tg} = \Sigma W_i/T_{gi}$$

wherein Wi is the weight fraction of each component I and Tgi is the glass transition temperature of each component i. To enhance the attainment of a composite Tg within the preferred range of about 250° K. to 275° K., it is desirable to employ both a liquid and a solid tackifier, even though this can be accomplished with a single semisolid tackifier.

The AB block copolymer can have any of a variety of configurations including linear triblock, star, radial, branched, and tapered geometries. The A block is rigid at the service temperature and preferably is styrene or alpha-methylstyrene. The B block is flexible at the service temperature and preferably is either a homopolymer of isoprene or butadiene or a copolymer of ethylene and butylene. The rigid A block preferably is present within the range of about 8% to 30% by weight of the total block copolymer when the B block is isoprene-based and about 20% to 50% by weight when the B block is butadiene-based.

Preferred AB block copolymers include ABA linear triblock copolymers of styrene and isoprene ranging from about 10% to about 21% styrene by weight such as those commercially available from Shell Chemical Company as Kraton ™ 1107 and 1111 or from Nippon-Zeon as Quintac ™ 3420, 3430, and 3530. Also preferred are ABA block copolymers of styrene and butadiene ranging from about 25% to 40% styrene by weight such as those commercially available from Firestone Synthetic Latex and Rubber Company as Stereon ™ 840A and 845A.

Preferred solid tackifying resins include rosin esters; hydrogenated rosin esters; polyterpene resins, polymerized hydrocarbon resins based on piperylene, isoprene, and other conjugated dienes containing 4 to 6 carbon atoms as well as hydrogenated versions of these materials; resins from polymerized and hydrogenated C9 hydrocarbon streams, resins from polymerized and hydrogenated cyclic dienes such as cyclopentadiene; resins from polymerized and hydrogenated pure monomer species such as styrene, vinyl toluene, and alpha-methylstyrene. Preferred solid tackifying resins include a hydrocarbon resin consisting essentially of polymerized structures derived primarily from a stream of aliphatic petroleum derivatives, both dienes and mono-olefins, containing 4 to 6 carbon atoms. Piperylene and isoprene are the most common species. Such resins are commercially available from Exxon Chemical Company as Escorez ™ 1310 and from the Goodyear Chemical Company as Wingtack Plus ™ and Wingtack ™ 95.

Preferred liquid tackifiers, sometimes referred to as plasticizers or softening agents, include liquid hydrocarbon resins and hydrogenated hydrocarbon resins, liquid polystyrenes, rosin oils, liquid rosin esters, liquid polyterpenes, liquid resins from polymerized and hydrogenated C9 hydrocarbon streams; liquid resins from polymerization and hydrogenation of a cyclic diene such as dicyclopentadiene; and liquid resins from polymerized and hydrogenated pure monomer species such as styrene, vinyl toluene, alpha-methylstyrene. Preferred liquid tackifyers include a liquid hydrocarbon resin consisting essentially of polymerized structures derived primarily from a stream of aliphatic petroleum derivatives, both dienes and monoolefins, containing 4 to 6 carbon atoms. One such resin is Wingtack ™ 10. Another class of liquid tackifyers can be produced from polymerized mixtures of aliphatic and aromatic monomers as exemplified by Escorez ™ 2520; such resins may be further hydrogenated. Another preferred liquid tackifyer is a polymerized alpha-pinene resin having a softening point around 25° C. available as Zonarez ™ A-25. Zonarez ™ A-25 is especially preferred for formulations containing styrene/butadiene block copolymers.

Other liquid tackifiers or plasticizers include naphthenic oils and paraffinic oils. The pressure-sensitive adhesive can also include commonly used additives such as antioxidants and fillers.

Figure 11:
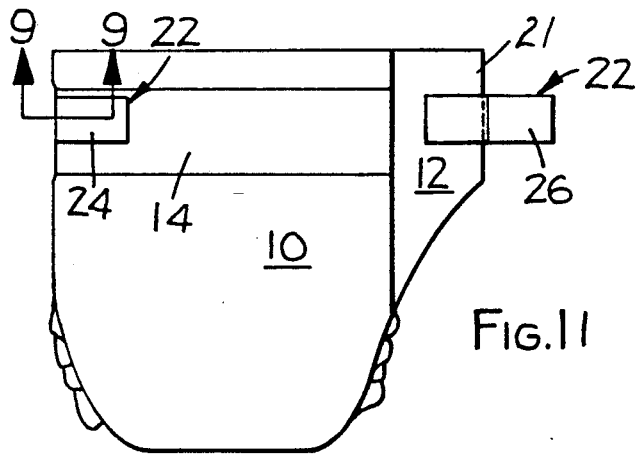
FIG. 11 is a schematic front view of a diaper having a refastenable adhesive closure of the invention.
Figure 12:
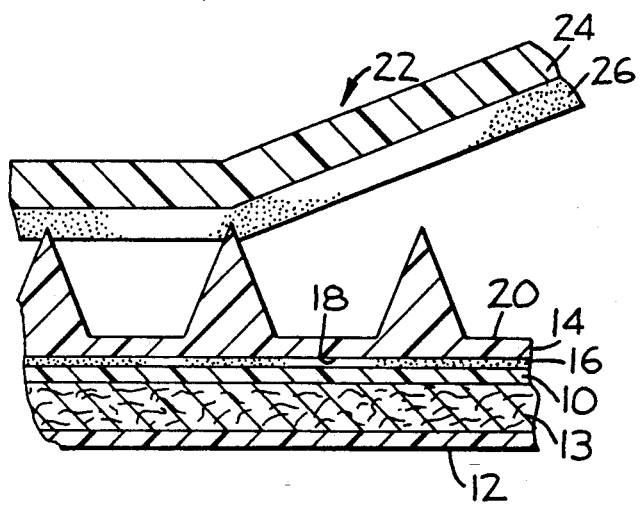
FIG. 12 is an enlarged cross section along line 9—9 of FIG. 11.
Figure 13:
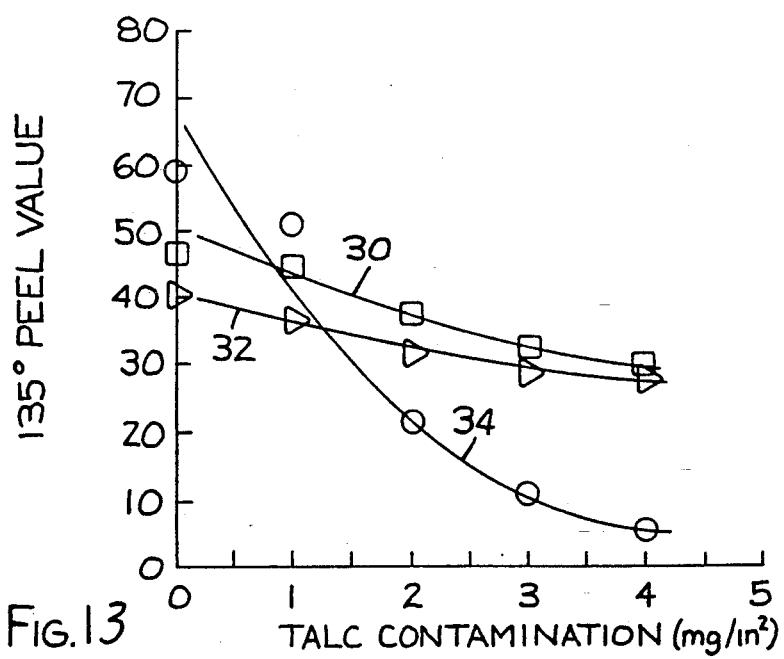
FIG. 13 is a graph illustrating the resistance of refastenable adhesive closures to contamination by talcum powder.

FIGS. 11 and 12 show an embodiment of the invention, i.e., the refastenable pressure-sensitive adhesive tape closure in use on a disposable diaper.

The diaper shown in FIGS. 11 and 12 has a water-impermeable cover or back sheet 10 and a water-permeable inner sheet 12, between which is an absorbent layer 13. A target strip 14 is adhered across the front of the cover sheet 10 by a layer of pressure-sensitive adhesive 16. The target strip has been cast to have a substantially flat under face 18 and an exposed face 20 in the form of peaks and valleys. The peaks extend across the full width of the target strip and crosswise to its length.

Permanently adhered to each ear 21 of the cover sheet 10 at the back of the diaper is a fastening tab 22 that has a flexible backing 24 and a layer of pressure-sensitive adhesive 26 by which the fastening tab is releasably adhered to the target strip.

The following non-limiting examples serve to illustrate the invention. In the following examples, all parts and percentages are by weight unless otherwise indicated.

The following tests are used in the examples and comparative examples for closure evaluation.

135° Peel Value

The resistance of a closure to a peel force at an angle of 135° is especially meaningful, because the fastener tab of a diaper may be peeled at that angle to open the closure.

This testing is carried out at constant temperature (23°±2° C.) and humidity (50±2% relative humidity) using a constant rate extension Instron TM tensile tester with a 135° test jig secured in the lower jaw. The target strip to be tested (5×12.5 cm) is adhered by a pressure-sensitive adhesive transfer tape to a steel panel. After attaching a 20 cm paper leader to a 2.54 cm wide pressure-sensitive fastening tab to be tested, the tab is centered over the target strip, adhesive side down, and immediately rolled lengthwise with one pass in each direction of a mechanically operated 4.5 lb (2.04 kg) hard-rubber roller. Within 15 seconds, the panel is slid into the jig slot, and the leader is clamped into the upper jaw. The chart is started at 12.5 cm/minute and the crosshead is started at 30 cm/minute to peel the fastening tab away. The peel value is read from the chart, disregarding the portion of trace due to removal of the initial and final 0.63 cm of the tab. The measurement is replicated at least twice and averaged. For a diaper closure that is not contaminated, the 135° peel value should be at least 10 N/dm, preferably at least 25 N/dm.

Test specimens were contaminated by talcum powder using a covered fluidized bed with a slit in the cover through which a smoke-like stream of the talcum powder was emitted. The test specimen was exposed to this stream and weighed before and after exposure.

SHEAR VALUE

The shear values were determined using modified PSTC-7 as follows. A target strip to be tested is reinforced by laminating to its non-test surface the adhesive layer of a pressure-sensitive adhesive tape having a 0.089 mm thick polypropylene backing (Y-8450 available from Minnesota Mining and Manufacturing Company). A fastening tab to be tested is laminated by its adhesive layer to the test surface of the target strip [1 inch by 1 inch (2.54 by 2.54 cm) test area]. After being allowed to dwell for 15 minutes in an air-circulating oven at 100° F. (38° C.), the bond to the polyolefin film is tested with a 1000 gram weight attached immediately. The time to fail is recorded, and the test is discontinued if no failure occurs within 1000 minutes. Reported values are averages of at least five tests. For a diaper closure that is not contaminated, the shear value should be at least 100 minutes.

PRESSURE-SENSITIVE ADHESIVES A-F

In the examples, pressure-sensitive adhesives were formulated from the following materials:

Kraton TM 1107 (Shell Chemical) ABA linear triblock copolymer of 14 parts styrene and 86 parts isoprene Kraton TM 1101 ABA linear triblock copolymer of 30 parts styrene and 70 parts butadiene Solprene TM 1205 (Fina) rubbery copolymer of styrene and butadiene Wingtack TM 10 (Goodyear Chemical) liquid tackifying resin based on C5 hydrocarbon olefins Wingtack Plus TM solid tackifying resin based on C5 hydrocarbon olefins Zonarez TM A-135 (Arizona Chemical) solid tackifying resin based on alpha-pinene Zonarez TM A-25 liquid tackifying resin based on alphapinene pinene Escorez TM 1301 (Exxon Chemical) solid C5 hydrocarbon tackifying resin Escorez TM 2520 mixed aliphatic/aromatic resin Escorez TM 5300 hydrogenated hydrocarbon solid tackifying resin Shellflex TM 371 (Shell Chemical) naphthenic oil Irganox TM 1076 (Ciba Geigy) antioxidant Pressure-sensitive Adhesives A-F were made from compositions of these materials as set forth in Table I, in parts by weight. The composite Tg of each composition was calculated and is also set forth in Table I.

TABLE I

|  | A | B | C | D | E | F |
|---|---|---|---|---|---|---|
| Kraton TM 1107 | 35 | 37 | 39.22 | 34.7 |  | 36 |
| Kraton TM 1101 |  |  |  |  | 11.23 |  |
| Solprene TM 1205 |  |  |  |  | 33.63 |  |
| Wingtack TM 10 | 16.5 | 26 |  |  |  |  |
| Wingtack Plus TM | 48.5 | 37 |  |  |  |  |
| Zonarez TM A-135 |  |  |  |  | 44.9 |  |
| Zonarez TM A-25 |  |  |  |  |  | 18 |
| Escorez TM 1310 |  |  |  |  |  | 46 |
| Escorez TM 2520 |  |  | 15.0 | 20.3 |  |  |
| Escorez TM 5300 |  |  | 43.82 | 44.1 |  |  |
| Shellflex TM 371 |  |  |  |  | 8.86 |  |
| Irganox TM 1076 | 1 | 1 | 1 | 1 | 1 | 1 |
| Tg | 263 | 255 | 263 | 265 | 275.2 | 261.8 |

TARGET STRIPS 1, 1A, 2-4, and 8

Target Strips 1, 1A and 2-4 were prepared by casting polyolefin film onto a casting roll maintained at 65° C., thus replicating the surface of the roll to produce a target strip, the working faces of which had peaks and valleys as illustrated in FIG. 1-4 of the drawing. Target Strip 8 was made in the same way and had peaks and valleys as illustrated in FIG. 12 of the drawing. The crown of each peak of Target Strips 1 and 1A had an angle of about 60°, one face of each peak was substantially orthogonal to the plane across the crowns of the peaks, the height of the peaks was 90 μm, and the distance between adjacent crowns was 160 μm. These dimensions and those of the other target strips are in Table I.

TARGET STRIPS 5-7

A flat nickel plate was machined to have peaks and valleys which were the mirror image of each of FIGS. 5-7 of the drawing. This was placed on the heated surface of a platen press (Sentinal ™ sealer), the temperature of which was 232° C. Low density polyethylene pellets were placed on the plate and covered with a silicone liner. The press was closed at a pressure of 90 psi (620 kPa) for two minutes. After cooling with water, the target strip 5, 6 or 7 (corresponding to FIG. 5, 6 or 7, respectively, of the drawing) was removed from the plate.

Key features of Target Strips 1, 1A, and 2-8 are tabulated in Table II together with a flat film of polypropylene that was used as a "control".

TABLE II

| Target Strip | FIG. of Drawing | Poly-olefin* | Casting Surface** | Thickness in μm Total | Peak to Valley | Peak Spacing in μm |
|---|---|---|---|---|---|---|
| 1 | 1 | PP | SS | 130 | 110 | 160 |
| 1A | 1 | PP/PE | SS | 130 | 110 | 160 |
| 2 | 2 | PP | Al | 95 | 70 | 140 |
| 3 | 3 | PP | SS | 100 | 80 | 160 |
| 4 | 4 | PP | Al | 95 | 70 | 210 |
| 5 | 5 | PE | Ni | 100 | 75 | 150 |
| 6 | 6 | PE | Ni | 250 | 200 | 150 |
| 7 | 7 | PE | Ni | 250 | 200 | 150 |
| 8 | 12 | PP | SS | 225 | 180 | 350 |
| Control | — | PP | CP | 50 | — | — |

*PP = polypropylene having a melt flow index of 35 g/10 min. (Escorene ™ PP-3085 from Exxon Chemical) extruded at about 275° C.
PE = polyethylene having a melt index of 3.7 (Norchem ™ NPE 1016) pressed at about 232° C.
PP/PE = blend of 60 parts propylene/ethylene impact copolymer having a melt flow index of 35 (WRS-7-319 from Shell Chemical) and 40 parts polyethylene homopolymer having a melt index of 3.5 (Tenite ™ 1550P from Eastman Chemical) extruded at about 296° C.
**SS = stainless steel with 1 mm copper coating which after being diamond turned, received an electroless nickel protective coating
CP = chromium plated stainless steel

TARGET STRIP ADHESIVE ROLL

Pressure-sensitive Adhesive F was hot-melt coated onto the smooth back face of long lengths of each of Target Strips 1-5 to a thickness of 20 μm. Each length was wound upon itself into a roll, each of which could be unwound without any offsetting of adhesive because of the reduced contact area between the face of the adhesive and the peaks of the target strip, even though no low-adhesion treatment had been applied to the uncoated face of the target strip.

FASTENING TAPES

Each of the Pressure-sensitive Adhesives A-F was hot-melt coated onto 75 μm polypropylene film which had been embossed to have a matte finish. The uncoated face of the polypropylene film had a low-adhesion backsize coating to permit the fastening tape to be wound upon itself in roll form.

EXAMPLES 1-11

A number of pressure-sensitive adhesive closures of the invention were made using Pressure-sensitive Adhesive D at a thickness of 50 μm on the fastening tape and one of Target Strips 1-8. These were tested for "135° Peel Value" at specified levels of contamination by talcum powder (Johnson & Johnson baby powder) and also for "Shear Value" without contamination.

Results are in Table III.

TABLE III

| Ex. | Target Strip | Direction of Force* | 135° Peel Values (N/dm) Talc Contamination (mg/6.45 cm²) | | | | | Shear Values (minutes) |
|---|---|---|---|---|---|---|---|---|
| | | | 0 | 1 | 2 | 3 | 4 | |
| | Control | — | 59 | 51 | 21 | 11 | 4 | >1000 |
| 1 | 1 | 1 | 46 | 44 | 39 | 32 | 30 | 800 |
| 2 | 1A | 1 | 40 | 32 | 24 | 19 | 16 | 764 |
| 3 | 1A | 2 | 32 | 26 | 21 | 16 | 13 | 200 |
| 4 | 2 | 1 | 66 | 50 | 40 | 30 | 23 | 755 |
| 5 | 2 | 2 | 44 | 35 | 19 | 10 | 8 | 310 |
| 6 | 3 | 1 | 40 | 36 | 31 | 29 | 27 | 389 |
| 7 | 4 | 1 | 54 | 47 | 29 | 20 | 15 | 795 |
| 8 | 5 | 2 | 33 | 70 | 64 | 40 | 31 | 590 |
| 9 | 6 | 1 | 13 | 5 | 1 | | | 140 |
| 10 | 7 | 1 | 22 | 16 | 1 | 7 | 4 | 10 |
| 11 | 8 | sym | 10 | 10 | 6 | 5 | 5 | 18 |

*1 = force applied in the same direction as the steep, or orthogonal, slopes of the peaks, i.e., As can be seen from the data in Table III, better peel values and shear values can be achieved when the working face of the target strip comprises saw-toothed ridges, Examples 1-7, or a configuration approaching saw-toothed ridges, Example 8. The peel values and shear values are further improved when the force applied to the closure is applied against orthogonal slopes of the peaks (direction 1), Examples 2 and 3 and Examples 4 and 5. The less preferred target strip working face configurations of Example 9 (ridges or ribs that are separated by square recessed surface portions having downwardly tapering sides), Example 10 (rounded peaks), and Example 11 (symmetrical peaks) provide lower peel values and shear values than do the saw-toothed ridges.

The 135° peel values of the "Control" of Table III are plotted as curve 34 of FIG. 10 of the drawing which graphically illustrates that its adhesion falls sharply upon being contaminated by talcum powder. The relatively horizontal slopes of curves 30 and 32 of FIG. 2, which respectively plot the 135° peel values of Examples 1 and 6, graphically illustrate far better resistance to contamination by talcum powder. Although curve 32 is somewhat more horizontal and hence more desirable than curve 30, the closure of Example 1 may be preferred because it exhibits a higher shear value. The difference in shear values is believed to result from the sharper crowns of the peaks of the target strips of Example 1, as compared to those of Example 6.

EXAMPLES 12-15

A series of refastenable closures were prepared as in Examples 1-11 using Target Strip 1A except changing the pressure-sensitive adhesive of the fastening tab. Each adhesive layer was 50 μm in thickness, and the backing of each fastening tab was polypropylene 75 μm in thickness. Test results in Direction 1 (see footnote of Table III) are reported in Table IV which includes shear values obtained when the target strip had been contaminated by about 1 mg/in² [1 mg/2.54 cm):] of talcum powder. The difference between 77 and 103 minutes for shear values of Example 14 is within experimental error.

TABLE IV

| Ex. | Adhesive | 135° Peel Values (N/dm) Talc Contamination (mg/6.45 cm$^2$) | | | | | Shear Value (minutes) Talc contamination (mg/6.45 cm$^2$) | |
| --- | --- | --- | --- | --- | --- | --- | --- | --- |
| | | 0 | 1 | 2 | 3 | 4 | 0 | 1 |
| 12 | B | 25 | 19 | 12 | 10 | 8 | 1 | 1 |
| Control* | B | 32 | 22 | 13 | 7 | 0 | 136 | 10 |
| 13 | C | 25 | 17 | 12 | 18 | 9 | >1000 | >1000 |
| Control* | C | 47 | 35 | 24 | 11 | 4 | >1000 | 881 |
| 14 | F | 40 | 31 | 24 | 22 | 17 | 77 | 103 |
| Control* | F | 68 | 46 | 29 | 17 | 14 | 781 | 48 |
| 15 | E | 36 | 29 | 25 | 19 | 17 | >1000 | 695 |
| 2 | D | 40 | 32 | 24 | 19 | 16 | 764 | 473 |

*Each Control employed the "Control" target strip of Table I

As can be seen from the data in Table IV, the closures of Examples 12–14 retain greater percentages of peel value and shear value than do the corresponding control closures as talc contamination is added. Although the shear value of the closure of Example 12 is low, such a closure would be useful as refastenable envelope closure since such closures are generally not subjected to shear forces. Where the closure is expected to be subjected to high shear forces, e.g., when the closure is intended for use as a disposable diaper closure, the closure of Example 13 using adhesive C would be preferred over the closure of Example 12. The peel values and shear values set forth for Examples 15 and restated for Example 2 demonstrate other adhesives which have excellent peel values and shear values both before and after contamination and which would be particularly useful in closures for disposable diapers.

Examples 16-20

A series of refastenable closures were prepared using Target Strip 2 having the height of the peaks above the valleys of 70 μm, and using fastening tabs carrying Pressure-sensitive Adhesives A or C at the thicknesses indicated in Table V.

Example 19 is a comparative example, the adhesive thickness being 100% of the height of the peaks above the valleys.

The peel values were determined for uncontaminated closures and for closures having various levels of contamination and the shear values were determined for uncontaminated closures, all tests being conducted with the force being applied in the same direction as the steep, or orthogonal, slopes of the peaks (direction 1). The results are set forth in Table V.

TABLE V

| Ex. | Adhesive | Thickness μm | 135° Peel Values (N/dm) Talc Contamination (mg/6.25 cm$^2$) | | | | | Shear Value (minutes) |
| --- | --- | --- | --- | --- | --- | --- | --- | --- |
| | | | 0 | 1 | 2 | 3 | 4 | No talcum |
| 16 | A | 17 | 7 | — | — | — | — | >1 |
| 17 | A | 33 | 27 | 24 | 22 | 21 | 19 | 16 |
| 18 | A | 50 | 74 | 50 | 35 | 27 | 23 | 40 |
| 19 | A | 70 | 85 | 63 | 49 | 39 | 30 | — |
| Control* | A | 50 | 63 | 46 | 27 | 17 | 11 | >1000 |
| 20 | C | 34 | 23 | 18 | 14 | 12 | 9 | 893 |

*The Control employed the "Control" target strip of Table II.

As can be seen from the data in Table V, that with the use of Adhesive A, adhesive thicknesses in the more preferred range of about 50 to 80% of the height of the peaks above the valleys (Example 17–47% and Example 18 71%) better peel values can be obtained than when the adhesive thicknesses are outside the more preferred range (Example 16–24%) and outside the required range (Example 19–100%).

The closures of Example 18 and the Control which have equal thickness of adhesive demonstrate the improved talc contamination resistance achieved in the closure of the invention, the closure of Example 18 having the peel value reduced to only 31% of the peel value of the uncontaminated closure on contamination with 4 mg/6.45 cm: talc, while the closure of the Control had the peel value reduced to 17% of the peel value of the uncontaminated closure on contamination with 4 mg/6.45 cm: talc The closures of Examples 17 and 20 demonstrate that selection of the adhesive composition affects both the peel values and the shear value at comparable thicknesses. While Adhesive A provides a closure having better peel values on contamination with talc (70% adhesion retention at 4 mg/6.25 cm$^2$ talc contamination) than does Adhesive C (39% adhesion retention at 4 mg/6.25 cm: talc contamination), Adhesive C provides a closure having a significantly better shear value than does Adhesive A.

The various modifications and alterations of this invention will be apparent to those skilled in the art without departing from the scope and spirit of this invention and this invention should not be restricted to that set forth herein for illustrative purposes.

We claim:

1. A refastenable closure comprising a pressure-sensitive adhesive-bearing fastening tab and a target portion having a working face for contact with said adhesive-bearing fastening tab, wherein
   said working face of said target strip is formed with peaks and valleys,
   the height of said peaks above said valleys being substantially uniform and from about 40 to 300 μm,
   the spacing between adjacent peaks being from about 50 to 500 μm,
   the back face of said target portion is substantially flat, and
   the thickness of the adhesive layer of said tab is no more than about 90% of the height of said peaks above said valleys.

2. The refastenable closure of claim 1 wherein said target portion is thermoplastic material.

3. The refastenable closure of claim 2 wherein said target portion is polyolefin.

4. The refastenable closure of claim 3 wherein said polyolefin is polypropylene, polyethylene, copolymers thereof or blends thereof.

5. The refastenable closure of claim 4 wherein said polyolefin is a blend of an ethylene/propylene copolymer and low density polyethylene.

6. The refastenable closure of claim 5 wherein said blend comprises about 50 to 80 weight percent ethylene/propylene copolymer having a melt flow index of about 10 to 100 g/10 min and 20 to 50 weight percent low density polyethylene having a melt index of about 1 to 50 g/10 min.

7. The refastenable closure of claim 1 wherein the crowns of said peaks are sharp.

8. The refastenable closure of claim 1 wherein the surface area of said peaks and valleys is at least 35% more than that of a flat surface, disregarding asperities less than 10 μm in height.

9. The refastenable closure of claim 1 wherein said target portion is permanently adhered to the body of an envelope and the fastening tab is permanently adhered to the flap of the envelope.

10. The refastenable closure of claim 1 wherein said target portion is permanently adhered to the front of the cover sheet of a diaper and said fastening tab is permanently adhered to each ear of the cover sheet at the back of the diaper.

11. The refastenable closure of claim 1 wherein said face of said target portion has a rough microstructure comprising closely spaced asperities that have a jagged appearance when viewed at a magnification of about 500 X and are about 2 to 30 μm in height and no more than 20% of the height of the peaks.

12. The refastenable closure of claim 1 wherein said target portion is a film strip sufficient in size that said portion covers said fastening tab and said back face of said target portion bears an adhesive.

13. The refastenable closure of claim 12 wherein said adhesive is a pressure-sensitive adhesive or a hot melt adhesive.

14. The refastenable closure of claim 1 wherein the thickness of the adhesive layer is at least about 25% of the height of the peaks.

15. The refastenable closure of claim 1 wherein the thickness of the adhesive layer is between about 50% to 80% of the height of the peaks.

16. A roll of tape useful for preparing the target portion of the closure of claim 1, said tape comprising a flexible polymeric substrate having a working face and an adhesive-bearing face, said working face having saw-toothed ridges, the height of said ridges above said substrate being substantially uniform and from about 40 to 300 μm, the spacing between adjacent ridges being from about 50 to 500 μm, said ridges having first and second faces transverse to the direction in which the tape is rolled or parallel to the direction in which the tape is rolled, said first transverse face being substantially orthogonal to said substrate, and the face bearing said adhesive being substantially flat.

17. A refastenable closure comprising a pressure-sensitive adhesive-bearing fastening tab and a target portion having a working face for contact with said adhesive-bearing fastening tab, wherein
said working face of said target strip is formed with peaks and valleys,
the height of said peaks above said valleys being substantially uniform and from about 40 to 300 μm,
the spacing between adjacent peaks being from about 50 to 500 μm,
said peaks have first and second faces transverse to the direction of removal of said fastening tab from said target portion,
the back face of said target portion is substantially flat, and
the thickness of the adhesive layer of said tab is no more than about 90% of the height of said peaks above said valleys.

18. The refastenable closure of claim 17 wherein said first transverse face is substantially orthogonal to said direction of removal.

19. The refastenable closure of claim 18 wherein said first transverse face faces away from said direction of removal.

20. The refastenable closure of claim 17 wherein said second face slopes downward from said peak.

21. The refastenable closure of claim 17 wherein said faces form angles of less than 90° at said peak.

22. The refastenable closure of claim 17 wherein said peaks form saw-toothed ridges, each extending across substantially the full width of the strip transversely to the direction of removal of the fastener tab from the target portion.

23. The refastenable closure of claim 22 having protrusions in the valleys that extend from 30 to 100% of the height of the peaks and are spaced apart from 0.2 to 6 mm.

24. The refastenable closure of claim 17 wherein the thickness of the adhesive layer is at least about 25% of the height of the peaks.

25. The refastenable closure of claim 17 wherein the thickness of the adhesive layer is between about 50% to 80% of the height of the peaks.

26. A disposable diaper comprising a water-impermeable cover sheet and a water-permeable inner sheet and absorbent layer between said cover sheet and said inner sheet, said diaper having front and back end portions with said back portion having ears protruding therefrom, target portions on said front portion of said cover sheet, and attached to each said ear a pressure-sensitive adhesive-bearing fastening tab, said target portions having a working face for contact with said adhesive-bearing fastening tab, wherein
said working face of said target strip is formed with peaks and valleys,
the height of said peaks above said valleys being substantially uniform and from about 40 to 300 μm,
the spacing between adjacent peaks being from about 50 to 500 μm,
the back face of said target portion is substantially flat, and
the thickness of the adhesive layer of said tab is no more than about 90% of the height of said peaks above said valleys.

27. A disposable diaper comprising a water-impermeable cover sheet and a water-permeable inner sheet and absorbent layer between said cover sheet and said inner sheet, said diaper having front and back end portions with said back portion having ears protruding therefrom, target portions on said front portion of said cover sheet, and attached to each said ear a pressure-sensitive adhesive-bearing fastening lab, said target portions having a working face for contact with said adhesive-bearing fastening tab, wherein
said target portions are provided as a unitary strip.
said working face of said target strip is formed with peaks and valleys, said peaks forming saw-toothed ridges, said ridges being oriented oppositely at the ends of the strip and extending across substantially the full width of the strip transversely to the direction of removal of the fastener tabs from the target portions,
the height of said peaks above said valleys being substantially uniform and from about 40 to 300 μm,
the spacing between adjacent peaks being from about 50 to 500 μm,
the back face of said target portion is substantially flat, and
the thickness of the adhesive layer of said tab is no more than about 90% of the height of said peaks above said valleys.

28. An envelope comprising a body and a flap, said flap bearing a pressure-sensitive adhesive-bearing fastening tab and said body bearing a target portion having a working face for contact with said adhesive-bearing fastening tab, wherein said working face of said target strip is formed with peaks and valleys, the height of said peaks above said valleys being substantially uniform and from about 40 to 300 μm, the spacing between adjacent peaks being from about 50 to 500 μm, the back face of said target portion is substantially flat, and the thickness of the adhesive layer of said tab is no more than about 90% of the height of said peaks above said valleys.

* * * * *

UNITED STATES PATENT AND TRADEMARK OFFICE
CERTIFICATE OF CORRECTION

PATENT NO. : 5,158,557

DATED : October 27, 1992

INVENTOR(S) : Allen L. Noreen, Dean R. Crissinger, William L. Melbye, Eric G. Rogers, Alan J. Sipinen and Leigh E. Wood It is certified that error appears in the above-identified patent and that said Letters Patent is hereby corrected as shown below:

| | |
|---|---|
| Col. 1, lines 9 and 40 | "closures" should read -- closures. -- |
| Col. 6, line 22 | insert -- . -- after "strength" |
| Col. 8, line 45 | "min preferably" should read -- min, preferably -- |
| Col. 8, line 49 | insert -- . -- after "strength" |
| Col. 12, line 25 | "alphapiene piene" should read -- alphapiene -- |
| Col. 14, line 21 | insert the following: |

--  ;

2 = force applied in the opposite direction as the steep, or orthogonal, slopes of the peaks, i.e.,

 ; and sym = symmetrical slope on peaks, i.e.,

 or  . --

UNITED STATES PATENT AND TRADEMARK OFFICE
CERTIFICATE OF CORRECTION

PATENT NO. : 5,158,557

DATED : October 27, 1992

INVENTOR(S) : Allen L. Noreen, Dean R. Crissinger, William L. Melbye
Eric G. Rogers, Alan J. Sipinen and Leigh E. Wood It is certified that error appears in the above-identified patent and that said Letters Patent is hereby corrected as shown below:

Col. 14, line 64     "cm):]" should read -- cm)$^2$] --

Col. 16, lines       "cm:" should read -- cm$^2$ --
9, 12 and 20

Signed and Sealed this

Twenty-fifth Day of January, 1994

Attest:

BRUCE LEHMAN

Attesting Officer    Commissioner of Patents and Trademarks